(12) United States Patent
Kuwano

(10) Patent No.: US 8,629,145 B2
(45) Date of Patent: *Jan. 14, 2014

(54) THERAPEUTIC AGENT FOR SPINAL CANAL STENOSIS

(75) Inventor: Keiichi Kuwano, Osaka (JP)

(73) Assignee: Nippon Shinyaku Co., Ltd., Kyoto (JP)

( * ) Notice: Subject to any disclaimer, the term of this patent is extended or adjusted under 35 U.S.C. 154(b) by 249 days.

This patent is subject to a terminal disclaimer.

(21) Appl. No.: 13/000,758

(22) PCT Filed: Jun. 22, 2009

(86) PCT No.: PCT/JP2009/061285
§ 371 (c)(1),
(2), (4) Date: Dec. 22, 2010

(87) PCT Pub. No.: WO2009/157396
PCT Pub. Date: Dec. 30, 2009

(65) Prior Publication Data
US 2011/0105518 A1 May 5, 2011

(30) Foreign Application Priority Data
Jun. 23, 2008 (JP) .................... 2008-162638

(51) Int. Cl.
  A61K 31/497 (2006.01)
  A01N 43/00 (2006.01)
  A01N 43/64 (2006.01)
  A61K 31/53 (2006.01)
  A61K 31/4965 (2006.01)

(52) U.S. Cl.
  USPC .................. 514/252.1; 514/217.05; 514/242; 514/255.05

(58) Field of Classification Search
  USPC ................. 514/252.1, 217.05, 242, 255.05
  See application file for complete search history.

(56) References Cited

U.S. PATENT DOCUMENTS

2004/0102436 A1 5/2004 Asaki et al.
2006/0069018 A1 3/2006 Sakai et al.

OTHER PUBLICATIONS

Tan (Singapore Med J, 2003, p. 168-169, 44(4)).*
PCT International Preliminary Report on Patentability for PCT/JP2009/061285 issued on Feb. 8, 2011.
Hideki Toyokawa, "Yobu Sekicyukan Kyosakusho no Shindan, Hozon Ryoho, Yobu Sekicyukan Kyosakusho no Yakubutsu Ryoho," Pain Clinic, 2001, vol. 22, No. 10, pp. 1362-1368.
Shinichi Konno, "Yobu Sekicyukan Kyosaku no. Hozon Ryoho," The Japanese Society of Lumber Spine Disorders, 2004, vol. 10, No. 1, pp. 10-13.
Keisuke Goto, et al., "Sekitsui Shikkan eno Approach Sekichukan Kyosakusho no Shindan to Chiryo," Gekkan Riumachika, 2003, vol. 29, No. 2, pp. 157-163.
Yoshifumi Takenobu, et al., "Establishment of an Walking Dysfunction Model Induced by the Compression of the Cauda Equina in the Rat," Kiso to Rinsho, vol. 30, No. 2, pp. 213-219, 1996.
Katsuhiko Nakai, et al., "The Effects of OP-1206 alpha-CD on Walking Dysfunction in the Rat Neuropathic Intermittent Claudication Model," Pain Medicine, 2002, 94, pp. 1537-1541.
Miho Sekiguchi, et al., "The Effects of Cilostazol on Nerve Conduction Velocity and Blood Flow; Acute and Chronic Cauda Equina Compression in a Canine Model," Spine, vol. 33, No. 24, 2008, pp. 2605-2611.
Tamaki Igarashi, et al., "Effects of acute nerve root compression on endoneurial fluid pressure and blood flow in rat dorsal root ganglia," Journal of Orthopaedic Research, 2005, 23, pp. 420-424.
Motohiro Inoue, et al., "Acupuncture Treatment for Low Back Pain and Lower Limb Symptoms—The Relation between Acupuncture or Electroacupuncture Stimulation and Sciatic Nerve Blood Flow," Evidenced-based complementary and alternative medicine 2008, 5, pp. 133-143.
H. Kato et al., Successful Treatment of Intermittent Claudication Due to Spinal Canal Stenosis Using Beraprost Sodium, a Stable Prostaglandin I2 Analogue, A Case Report, Angiology, The Journal of Vascular Diseases, vol. 48, No. 5, May 1997, pp. 457-461.
K. Kuwano et al., 2-{4-[5,6-Diphenylpyrazin-2-yl)(isopropyl)amino]butoxy}-N-(methylsulfonyl)acetamide (NS-304), an Orally Available and Long-Acting Prostacyclin Receptor Agonist Prodrug, The Journal of Pharmacology and Experimental Therapeutics, vol. 332, No. 3, 2007, pp. 1181-1188.

* cited by examiner

Primary Examiner — Sreeni Padmanabhan
Assistant Examiner — Uma Ramachandran
(74) Attorney, Agent, or Firm — McDermott Will & Emery LLP

(57) ABSTRACT

The main object of the present invention is to provide a novel agent for the treatment of spinal canal stenosis.

The present invention relates to an agent for the treatment of spinal canal stenosis containing the heterocyclic derivative represented by the following general formula (1) or a pharmaceutically acceptable salt thereof as an active ingredient;

[chem. 1]

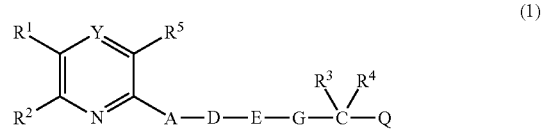

(1)

In the formula (1),
  $R^1$ and $R^2$ are the same or different and each represents an optionally substituted aryl;
  $R^3$ and $R^4$ are the same or different and each represents hydrogen atom or alkyl;
  $R^5$ represents hydrogen atom, alkyl or halogen atom;
  Y represents N or N→O;
  A represents $NR^6$, and $R^6$ represents hydrogen atom, alkyl, etc.;
  D represents alkylene or alkenylene which is optionally substituted with hydroxy;
  E represents phenylene or a single bond;
  G represents O, S, etc.; and
  Q represents carboxy, alkoxycarbonyl, etc.

3 Claims, 1 Drawing Sheet

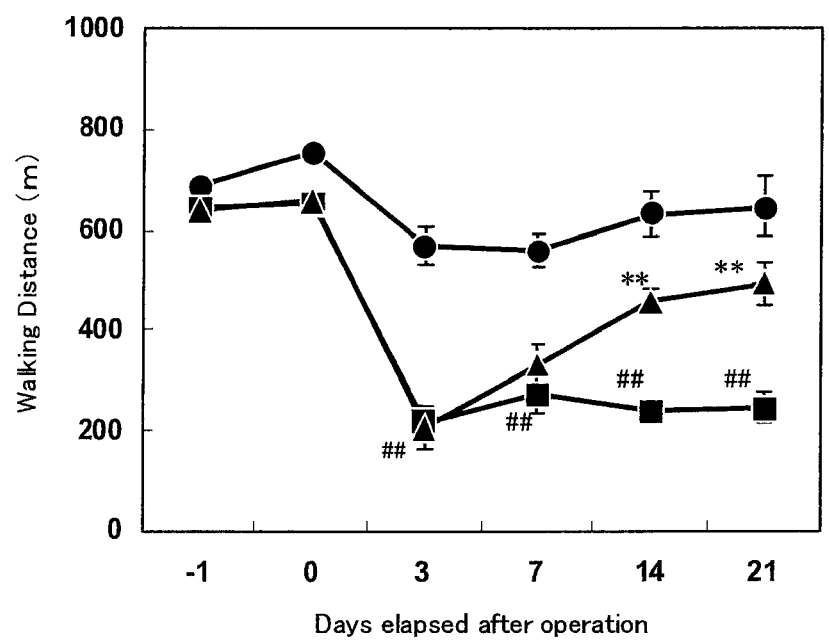

THERAPEUTIC AGENT FOR SPINAL CANAL STENOSIS

CROSS REFERENCE TO PRIOR APPLICATIONS

This application is a U.S. National Phase application under 35 U.S.C. §371 of International Application No. PCT/JP2009/061285, filed on Jun. 22, 2009 and claims benefit of priority to Japanese Patent Application No. 2008-162638, filed on Jun. 23, 2008. The International Application was published in Japanese on Dec. 30, 2009 as WO 2009/157396 A1 under PCT Article 21(2). The contents of these applications are hereby incorporated by reference.

TECHNICAL FIELD

The present invention relates to an agent for treatment of spinal canal stenosis containing a heterocyclic derivative (hereinafter, referred to as "the present heterocyclic derivative (1)") represented by the following general formula (1) or a pharmaceutically acceptable salt thereof as an active ingredient;

[chem. 1]

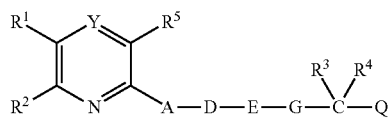

(1)

In the formula (1), $R^1$ and $R^2$ are the same or different and each represents an optionally substituted aryl, and the substituents are the same or different and one to three substituents are selected from the group consisting of halogen atom, alkyl, haloalkyl, arylalkyl, alkoxy, alkylthio, alkoxyalkyl, alkylsulfonyl, hydroxy, amino, monoalkylamino, dialkylamino, carboxy, cyano and nitro;

$R^3$ and $R^4$ are the same or different and each represents hydrogen atom or alkyl;

$R^5$ represents hydrogen atom, alkyl or halogen atom;

Y represents N or N→O;

A represents $NR^6$, and $R^6$ represents hydrogen atom, alkyl, alkenyl or cycloalkyl;

D represents alkylene or alkenylene which is optionally substituted with hydroxy, or A and D are combined with each other to form a divalent group represented by the following formula (2)

[chem. 2]

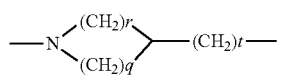

(2)

[In the formula (2), r represents an integer of 0 to 2, q represents 2 or 3 and t represents an integer of 0 to 4];

E represents phenylene or a single bond, or D and E are combined with each other to form a divalent group represented by the following formula (3)

[chem. 3]

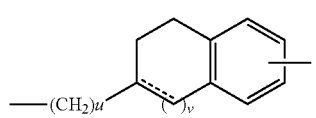

(3)

($\text{---}$ represents a single bond or a double bond.)

[In the formula (3), u represents an integer of 0 to 2 and v represents 0 or 1];

G represents O, S, SO or $SO_2$; and

Q represents carboxy, alkoxycarbonyl, tetrazolyl, carbamoyl, monoalkylcarbamoyl, dialkylcarbamoyl or the group represented by the following formula (4).

[chem. 4]

(4)

[In the formula (4), $R^7$ represents amino, monoalkylamino, dialkylamino, hydroxy, any of the group of the following 1) to 4) which are optionally substituted with 1 to 3 substituents selected from the group consisting of halogen atom, alkyl, haloalkyl, arylalkyl, alkoxy, alkylthio, alkoxyalkyl, alkylsulfonyl, hydroxy, amino, monoalkylamino, dialkylamino, carboxy, cyano and nitro;
1) alkyl,
2) aryl,
3) aryloxy, and
4) heterocyclic group.]

BACKGROUND ART

Spinal canal stenosis is a disease of various symptoms that appear due to compression of nerve tissues such as nerve root or cauda equina, as a result of narrowing of spinal canal caused by the hypertrophic degeneration of spine or ligamentum flavum constituting spinal canal, or the projection of intervertebral disk. Depending upon the stenosed site, spinal canal stenosis is classified as cervical spinal canal stenosis, thoracic spinal canal stenosis, lumbar spinal canal stenosis, diffuse spinal canal stenosis, sacral stenosis, etc. Examples of the symptom thereof are lumbago, pain of lower limbs, numbness, etc. due to nerve compression. Especially in the case of cauda equina compression, symptoms of lumbago, pain in lower limbs, numbness, cataplectic feeling become severe during walking.

As a treating agent for lumbar spinal canal stenosis which is one of spinal canal stenosis, limaprost which is a derivative of prostaglandin $E_1$ has been known and used for the improvement in subjective symptoms of lumbar spinal canal stenosis (such as pain or numbness of lower limbs) and in walking ability.

On the other hand, the present heterocyclic derivative (1) or a pharmaceutically acceptable salt thereof has already been reported to be useful for the treatment of pulmonary hypertension or obstructive arteriosclerosis as a $PGI_2$ receptor agonist (see, for example, Patent Document 1).

Patent Document 1: Pamphlet of International Publication WO 02/088084

DISCLOSURE OF THE INVENTION

Problems that the Invention is to Solve

The main object of the present invention is to provide a novel agent for the treatment of spinal canal stenosis.

Means for Solving the Problems

The present inventor has found that the present heterocyclic derivative (1) is able to improve the gait disturbance caused by compression of cauda equina in rats and achieved the present invention.

An example of the present invention is an agent for the treatment of spinal canal stenosis containing the present heterocyclic derivative (1) or a pharmaceutically acceptable salt thereof as an active ingredient.

BRIEF DESCRIPTION OF THE DRAWING

[FIG. 1]

FIG. 1 shows the effect of 2-{4-[N-(5,6-diphenylpyrazin-2-yl)-N-isopropylamino]butyloxy}-N-(methylsulfonyl)acetamide (hereinafter, referred to as "the compound A") for improving the walking disability in the model rats suffering from walking disability due to compression of cauda equina. An ordinate shows the walking distance (m) and an abscissa shows the elapsed days after the operation. In the drawing, circular, square and triangular marks represent sham operation group, control group and drug-administered group, respectively.

BEST MODE FOR CARRYING OUT THE INVENTION

In the present heterocyclic derivative (1), the preferred one is that where $R^1$ and $R^2$ are the same or different and each represents optionally substituted phenyl, and the substituents are the same or different and one to three substituents selected from the group consisting of halogen atom, alkyl and alkoxy;

$R^3$ and $R^4$ are the same or different and each represents hydrogen atom or alkyl;

$R^5$ represents hydrogen atom;

Y represents N;

A represents $NR^6$, and $R^6$ represents alkyl;

D represents alkylene;

E represents a single bond;

G represents O; and

Q represents carboxy or a group represented by the following formula (4), and $R^7$ represents amino, monoalkylamino, dialkylamino, hydroxy, or any of the group of the following 1) to 4) which are optionally substituted with 1 to 3 substituents selected from the group consisting of halogen atom, alkyl, haloalkyl, arylalkyl, alkoxy, alkylthio, alkoxyalkyl, alkylsulfonyl, hydroxy, amino, monoalkylamino, dialkylamino, carboxy, cyano and nitro;

1) alkyl,
2) aryl,
3) aryloxy, and
4) heterocyclic group.

To be more specific, the compound A and 2-{4-[N-(5,6-diphenylpyrazin-2-yl)-N-isopropylamino]butyloxy}acetic acid (hereinafter, referred to as "the compound B") are preferable for example.

As to the "alkyl" in the present invention, that which is straight or branched having 1 to 6 carbon atoms, for example, methyl, ethyl, n-propyl, isopropyl, n-butyl, isobutyl, sec-butyl, tert-butyl, n-pentyl, isopentyl, n-hexyl or isohexyl may be exemplified. Particularly, alkyl having 1 to 4 carbon atoms is preferable.

As to an alkyl moiety in "haloalkyl", "arylalkyl", "alkylthio", "alkoxyalkyl", "alkylsulfonyl", "monoalkylamino", "dialkylamino", "monoalkylcarbazoyl" and "dialkylcarbamoyl" in the present invention, that which is the same as the already-mentioned alkyl may be exemplified.

As to the "alkoxy" in the present invention, that which is straight or branched having 1 to 6 carbon atoms, for example, methoxy, ethoxy, n-propoxy, isopropoxy, n-butoxy, isobutoxy, sec-butoxy, tert-butoxy, n-pentyloxy, isopentyloxy, n-hexyloxy or isohexyloxy may be exemplified. Particularly, alkoxy having 1 to 4 carbon atoms is preferable.

As to an alkoxy moiety in "alkoxycarbonyl" and "alkoxyalkyl" in the present invention, that which is the same as the already-mentioned alkoxy may be exemplified.

As to the "alkenyl" in the present invention, that which is straight or branched having 2 to 6 carbon atoms, for example, vinyl, 1-propenyl, 2-propenyl, 1-butenyl, 2-butenyl, 3-butenyl, 1-pentenyl, 2-pentenyl, 3-pentenyl, 4-pentenyl, 4-methyl-3-pentenyl, 1-hexenyl, 2-hexenyl, 3-hexenyl, 4-henexyl or 5-hexenyl may be exemplified. Particularly, alkenyl having 3 or 4 carbon atoms is preferable.

As to the "cycloalkyl" in the present invention, that which has 3 to 8 carbon atoms, for example, cyclopropyl, cyclobutyl, cyclopentyl, cyclohexyl, cycloheptyl or cyclooctyl may be exemplified. Particularly, cycloalkylo having 5 to 7 carbon atoms is preferable.

As to the "halogen atom" in the present invention, fluorine atom, chlorine atom, bromine atom and iodine atom may be exemplified.

As to the "aryl" in the present invention, that which has 6 to 10 carbon atoms, for example, phenyl, 1-naphthyl or 2-naphthyl may be exemplified. Particularly, phenyl is preferable.

As to the aryl moiety in "arylalkyl" and "aryloxy" in the present invention, that which is the same as in the already-mentioned aryl may be exemplified.

As to the "alkylene" in the present invention, that which is straight or branched having 1 to 8 carbon atoms, for example, methylene, ethylene, 1-methylethylene, 2-methylethylene, trimethylene, tetramethylene, pentamethylene, hexamethylene, heptamethylene or octamethylene may be exemplified. Particularly, alkylene having 3 to 6 carbon atoms is preferable, and alkylene having 4 carbon atoms is more preferable.

As to the "alkenylene" in the present invention, that which is straight or branched having 2 to 8 carbon atoms, for example, ethenylene, 1-propenylene, 2-propenylene, 1-butenylene, 2-butenylene, 3-butenylene, 1-pentenylene, 2-pentenylene, 3-pentenylene, 4-pentenylene, 4-methyl-3-pentenylene, 1-hexenylene, 2-hexenylene, 3-hexenylene, 4-hexenylene, 5-hexenylene, 1-heptenylene, 2-heptenylene, 3-heptenylene, 4-heptenylene, 5-heptenylene, 6-heptenylene, 1-octenylene, 2-octenylene, 3-octenylene, 4-octenylene, 5-octenylene, 6-octenylene or 7-octenylene may be exemplified. Particularly, alkenylene having 3 to 6 carbon atoms is preferable, and alkenylene having 4 carbon atoms is more preferable.

As to the "heterocyclic group" in the present invention, the following (1) or (2) may be exemplified.

(1) A five- to six-membered aromatic ring group having 1 to 4 hetero atoms selected from nitrogen atom, oxygen atom and sulfur atom, or a benzene condensed ring thereof and nitrogen atom and sulfur atom may form an oxide when a ring-constituent atom is nitrogen atom or sulfur atom. Examples thereof include 1-pyrrolyl, 2-pyrrolyl, 3-pyrrolyl, 3-indolyl, 2-furanyl, 3-furanyl, 3-benzofuranyl, 2-thienyl, 3-thienyl, 3-benzothienyl, 1,3-oxazol-2-yl, 4-isoxazolyl, 2-thiazolyl, 5-thiazolyl, 2-benzothiazolyl, 1-imidazolyl, 2-imidazolyl, 4-imidazolyl, 2-benzimidaolyl, 1H-1,2,4-triazol-1-yl, 1H-tetrazol-5-yl, 2H-tetrazol-5-yl, 2-pyridyl, 3-pyridyl, 4-pyridyl, 3-pyrazolyl, 2-pyrimidinyl 4-pyrimidinyl, 2-pyrazinyl, and 1,3,5-triazin-2-yl.

(2) A four- to eight-membered saturated ring group which optionally has one to four same or different nitrogen atom, oxygen atom or sulfer atom, or a benzene condensed ring thereof, and nitrogen atom and sulfer atom may form an oxide when a ring-constituent atom is nitrogen atom or sulfer atom. Examples thereof include piperidino, piperazinyl, 3-methylpiperazin-1-yl, homopiperazinyl, morpholino, thiomorpholino, 1-pyrrolidinyl, 2-pyrrolidinyl and 2-tetrahydrofuranyl.

The present heterocyclic derivative (1) is able to be synthesized by the process mentioned in the above-mentioned Patent Document 1 (pamphlet of International Publication WO 02/088084).

Although the present heterocyclic derivative (1) may be used as a pharmaceutical just in a form of free base or acid, it is also possible to use by making into a form of a pharmaceutically acceptable salt by a known method.

Examples of the "salt" when the present heterocyclic derivative (1) shows basicity include a salt with inorganic acid such as hydrochloric acid, sulfuric acid, nitric acid, phosphoric acid, hydrofluoric acid or hydrobromic acid and with organic acid such as acetic acid, tartaric acid, lactic acid, citric acid, fumaric acid, maleic acid, succinic acid, methanesulfonic acid, ethanesulfonic acid, benzenesulfonic acid, p-toluenesulfonic acid, naphthalenesulfonic acid or camphorsulfonic acid.

Examples of the "salt" when the present heterocyclic derivative (1) shows acidity include alkali metal salt such as sodium salt or potassium salt and alkali earth metal salt such as calcium salt.

There are geometrical isomers (Z and E substances) in the present heterocyclic derivative (1) and each of the geometrical isomers and a mixture thereof are also included in the present heterocyclic derivative (1). Some of the present heterocyclic derivative (1) has asymmetric carbon(s) and each of optical isomers and racemic substance thereof are also included in the present heterocyclic derivative (1). An optical isomer is able to be produced by subjecting the racemic substance prepared as above to an optical resolution by a known method using an optically active acid (such as tartaric acid, benzoyltartaric acid, mandelic acid or 10-camphorsulfonic acid) utilizing the basicity or by using a previously-prepared optically active compound as a material.

The agent for the treatment of spinal canal stenosis of the present invention is able to be used for the purpose of improving the symptoms such as paralysis, dullness in sensory perception, pain, numbness, lowering in walking ability, etc. associated with cervical spinal canal stenosis, thoracic spinal canal stenosis, lumbar spinal canal stenosis, diffuse spinal canal stenosis or sacral stenosis. The agent is particularly preferred to the symptoms associated with lumbar spinal canal stenosis (such as pain or numbness of lower limbs or lowering in walking ability).

The agent for the treatment of spinal canal stenosis of the present invention is the present heterocyclic derivative (1) as it is or is the agent containing the derivative in a pharmaceutically acceptable, nontoxic and inert carrier at a rate ranging from 0.01 to 99.5% or, preferably, ranging from of 0.5 to 90%.

Examples of the carrier include solid, semi-solid or liquid diluent, filler and other auxiliary agents for pharmaceutical formulation. These can be used alone or as a mixture of two or more thereof.

The agent for the treatment of spinal canal stenosis of the present invention may be in any of the forms of oral preparations such as powder, capsules, tablets, sugar-coated tablets, granules, diluted powder, suspension, liquid, syrup, elixir or troche and parenteral preparations such as injection or suppository in a solid or liquid dose unit. It may also be in a form of a sustained release preparation. Among them, oral preparations such as tablets are particularly preferable.

Powder is able to be manufactured by making the present heterocyclic derivative (1) into an appropriate fine size.

Diluted powder is able to be manufactured by such a manner that the present heterocyclic derivative (1) is made into an appropriate fine size and then mixed with a pharmaceutical carrier which is similarly made into the fine size such as edible carbohydrate (e.g., starch and mannitol). Flavoring agent, preservative, dispersing agent, coloring agent, perfume, etc. may be optionally added thereto.

Capsules are able to be manufactured by such a manner that the powder or diluted powder which is made powdery as mentioned above or granules which will be mentioned under the item for tablets is/are filled in an capsule shell such as gelatin capsule. It is also possible to manufacture in such a manner that the powder or the diluted powder in a powdery form is mixed with a lubricant or a fluidizing agent such as colloidal silica, talc, magnesium stearate, calcium stearate or solid polyethylene glycol followed by subjecting to a filling operation. When a disintegrating agent or solubilizing agent such as carboxymethyl cellulose, carboxymethyl cellulose calcium, lowly-substituted hydroxypropyl cellulose, croscarmellose sodium, carboxymethyl starch sodium, calcium carbonate or sodium carbonate is added, efficacy of the pharmaceutical when the capsules are ingested is able to be improved. It is also possible that fine powder of the present heterocyclic derivative (1) is suspended/dispersed in vegetable oil, polyethylene glycol, glycerol or surfactant and wrapped with a gelatin sheet to give a soft capsule preparation.

Tablets are able to be manufactured in such a manner that a powdery mixture is prepared by addition of a filler to the present heterocyclic derivative (1) which was made powdery and made into granules or slugs and then a disintegrating agent or a lubricant is added thereto followed by making into tablets. The powdery mixture is able to be manufactured by mixing an appropriately powdered heterocyclic derivative (1) with a diluent or a base. If necessary, it is possible to add a binder (such as carboxymethyl cellulose sodium, methyl cellulose, hydroxypropyl methyl cellulose, gelatin, polyvinylpyrrolidone or polyvinyl alcohol), a dissolution retarding agent (such as paraffin), a reabsorbing agent (such as a quaternary salt), an adsorbent (such as bentonite or kaolin), etc. thereto.

The powdery mixture is able to be made into granules in such a manner that it is firstly made wet using binder, for example, syrup, starch paste, acacia, cellulose solution or polymer solution, mixed with stirring and dried followed by grinding. Instead of making the powder into granules as such, it is also possible that the powder is applied to a tabletting machine and the resulting slug in an incomplete shape is ground to give granules. When a lubricant such as stearic acid, stearate, talc or mineral oil is added to the granules prepared as such, sticking of the granules each other is able to be prevented.

Tablets are also able to be manufactured in such a manner that the present heterocyclic derivative (1) is mixed with a fluid inert carrier and then directly making into tablets without conducting the above steps of making into granules or slugs.

The tablets prepared as such are able to be subjected to film coating or sugar coating. It is also possible to apply a transparent or semi-transparent protective coat comprising a tightly closed shellac film, a coat comprising sugar or polymer material, or a polished coat comprising wax.

In other oral preparation such as liquid, syrup, troche or elixir, it is also possible to make into a dose unit form where a predetermined amount thereof contains a predetermined amount of the present heterocyclic derivative (1).

The syrup is able to be manufactured by dissolving the present heterocyclic derivative (1) into an appropriate aqueous solution of flavor. The elixir is able to be manufactured using a non-toxic alcoholic carrier.

The suspension is able to be manufactured by dispersing the present heterocyclic derivative (1) into a non-toxic carrier. If necessary, it is possible to add a solubilizing agent or an emulsifier (such as ethoxylated isostearyl alcohol or polyoxyethylene sorbitol ester), a preservative or a flavor-endowing agent (such as peppermint oil or saccharine) thereto.

If necessary, the dose unit formulation for oral administration may be made into microcapsules. The formulation is also able to be coated or embedded into polymer or wax to obtain a prolonged action or sustained release of the active ingredient.

The parenteral preparation is able to be in a liquid dose unit form for subcutaneous, intramuscular or intravenous injection such as in a form of solution or suspension. The parenteral preparation is able to be manufactured in such a manner that a predetermined amount of the present heterocyclic derivative (1) is suspended or dissolved into a non-toxic liquid carrier meeting the purpose of injection such as aqueous or oily medium and then the suspension or solution is sterilized. Non-toxic salt or a solution thereof may be added thereto for making the injection solution isotonic. It is also possible to add a stabilizer, a preservative, an emulsifier and the like.

The suppository is able to be manufactured by dissolving or suspending the present heterocyclic derivative (1) into a low-melting and water-soluble or insoluble solid such as polyethylene glycol, cacao fat, semi-synthetic fat/oil (such as Witepsol (registered trade mark)), higher ester (such as myristyl palmitate ester) or a mixture thereof.

Although the dose of the agent for the treatment of spinal canal stenosis of the present invention may vary depending upon the state of a patient such as body weight or age, administering route or degree of symptom, a range of 0.001 mg to 100 mg/day as an amount of the present heterocyclic derivative (1) is generally suitable for an adult and a range of 0.01 mg to 10 mg is more preferable. In some cases, the dose less than the above may be sufficient or, on the other hand, the dose more than the above may be necessary. It is also possible to administer one to several times a day or to administer with an interval of one to several days.

EXAMPLES

The present invention will now be illustrated in more detail by way of the following test examples although the present invention is not limited to the scope mentioned in the following range.

Test Example 1

(1) Methods

Wistar strain rats (male; seven weeks age) (Charles Liver Japan) were subjected to a walk training once daily for continuous three or four days using a treadmill (manufactured by Muromachi Kikai). On the last day of the walk training, the animals were grouped and, on the next day, the walking time was measured and then a sham operation or an operation for compressing the cauda equina mentioned below i) was carried out. On the third, seventh, fourteenth and twenty-first days after the operation, walking time was measured. Based on the walking time measured, a walking distance was calculated.

After measuring the walking time on the third day, the group for which the operation for compressing the cauda equina was carried out was further grouped into a control group and a drug-administered group on the basis of their walking distances on the day when the operation was done and on the third day after the operation.

After that, a 0.5 w/v % aqueous solution of methyl cellulose was orally administered to the sham operation group and the control group twice daily until the 13th or the 20th day after the operation while a suspension containing 0.2 mg/mL of the compound A (medium: 0.5 w/v % aqueous methyl cellulose solution) was orally administered to the drug-administered group in the same manner.

i) Method for the Operation for Compressing the Cauda Equina

The operation for compressing the cauda equina was carried out in accordance with a method of Takenobu, et al. (*Kiso to Rinsho*, vol. 30, pages 213 to 219, 1996).

Rats were anesthetized with pentobarbital sodium, hair of the back was shaved, the lumbar area was incised and the area from the fourth to the sixth lumbar vertebrae was exposed. After the fifth lumbar spinous process was excised, holes of an appropriate size for insertion of silicone rubber (height×length×width=1×4×1.25 mm) were formed using a hand piece installed with diamond bar (manufactured by Miniter) on two places (near the boundary between the fourth and the fifth lumbar vertebrae and near the boundary between the fifth and the sixth lumbar vertebrae). After silicone rubber was inserted into each of the fourth and the sixth lumbar vertebral canals, the excised site was sutured. The same operation was also conducted for the sham operation group and the excised site was sutured without insertion of silicone rubber. The sutured site was applied with an appropriate amount of Terramycin (manufactured by Pfizer). Further, Viccillin S for injection (manufactured by Meiji Seika) was dissolved in 2.5 mL of a physiological saline solution (manufactured by Otsuka Seiyaku) and 0.5 mL thereof was intramuscularly injected into the hind limb.

ii) Method for Measuring the Walking Time

Three to five rats were placed on a running belt in a horizontal state and the running belt was driven. A program was set up in such a manner that the treadmill was firstly driven at the speed of 10 m/min and accelerated to an extent of 5 m/min every three minutes and, after an operation for 30 minutes, the treadmill was automatically stopped. Acceleration at the driving and speed-changing stages was 1 m/sec$^2$ and it was considered that the acceleration was immediately done and reached the next speed. When the rats completely got on the electric stimulation device, it was judged that the walking became impossible and the time from the driving of the treadmill until the impossible walking was defined as the walking time. Walking time of a rat which continued the walking for 30 minutes was defined as 30 minutes.

iii) Method for Walk Training

The treadmill was operated and walking time of each rat was measured using a timer. When the walking time was shorter than 24 minutes, the rat was forced to continue walking so as to raise the training effect and, at the stage when the walking became impossible again after 24 minutes, the training for the rat was finished.

(2) Results

As shown in FIG. 1, disability in walking due to compression of cauda equina was significantly improved when the compound A was administered.

As to the evaluation, the control group was evaluated by a Welch test against the sham operation group (##: p<0.01).

The drug-administered group was evaluated by a t-test or a Welch test against the control group (★★: p<0.01).

Test Example 2

Spinal canal stenosis rat model is generated by version of the method described in the document (Pain Medicine 2002; 94: 1537-41). Afterwards, the rat is administered the compound A or the compound B, and a change in spinal cord blood flow is determined to evaluate the therapeutic effect of the compound A or the compound B.

Test Example 3

Cauda equina compression dog model is generated by version of the method described in the document (SPINE 2008; 33: 2605-11). Afterwards, the dog is administered the compound A or the compound B, and a change in nerve-conduction velocity or cauda equina blood flow is determined to evaluate the therapeutic effect of the compound A or the compound B.

Test Example 4

L5 nerve root compression rat model is generated by version of the method described in the document (J Orthopaedic Research 2005; 23: 420-24). Afterwards, the rat is administered the compound A or the compound B, and a change in dorsal root ganglion blood flow is determined to evaluate the therapeutic effect of the compound A or the compound B.

Test Example 5

A rat is administered the compound A or the compound B. Afterwards, a change in sciatic nerve blood flow is determined by version of the method described in the document (Evidence-based complementary and alternative medicine 2008; 5: 133-43) to evaluate the therapeutic effect of the compound A or the compound B.

The invention claimed is:

1. A method for treating spinal canal stenosis in a patient comprising administering an agent containing 2-{4-[N-(5,6-diphenylpyrazin-2-yl)-N-isopropylamino]butyloxy}acetic acid or 2-{-4-[N-(5,6-diphenylpyrazin-2-yl)-N-isopropylamino]butyloxy}-N-(methylsulfonyl)acetamide, or a pharmaceutically acceptable salt thereof to the patient in an amount of 0.001 mg to 100 mg/day.

2. The method according to claim 1, wherein the spinal canal stenosis is cervical spinal canal stenosis, thoracic spinal canal stenosis, lumbar spinal canal stenosis, diffuse spinal canal stenosis or sacral stenosis.

3. The method according to claim 1, wherein the spinal canal stenosis is lumbar spinal canal stenosis.

\* \* \* \* \*